(12) United States Patent
Beckers et al.

(10) Patent No.: US 6,462,209 B1
(45) Date of Patent: Oct. 8, 2002

(54) PROCESS FOR THE PURIFICATION OF PROPYLENE OXIDE

(75) Inventors: Johannes Gerhardus Joseph Beckers, Amsterdam (NL); Johannes Jozias Blom, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/936,650

(22) PCT Filed: Mar. 14, 2000

(86) PCT No.: PCT/EP00/02272

§ 371 (c)(1),
(2), (4) Date: Sep. 14, 2001

(87) PCT Pub. No.: WO00/55148

PCT Pub. Date: Sep. 21, 2000

(30) Foreign Application Priority Data

Mar. 16, 1999 (EP) .............................................. 99200810

(51) Int. Cl.[7] ............................................ C07D 301/32
(52) U.S. Cl. ......................................................... 549/542
(58) Field of Search .......................................... 549/542

(56) References Cited

FOREIGN PATENT DOCUMENTS

| EP | 0 275 680 A1 | 7/1988 | ......... C07D/301/32 |
|---|---|---|---|
| EP | 0 601 273 A1 | 12/1992 | ......... C07D/301/32 |
| EP | 0 736 528 A1 | 3/1995 | ......... C07D/301/32 |

OTHER PUBLICATIONS

Patent abstracts of Japan vol. 1997, No. 2, Feb. 28, 1997, JP 08 283253 A, Oct. 19, 1996, Japan, C07D, 301/32.

*Primary Examiner*—T. A. Solola
(74) *Attorney, Agent, or Firm*—Y. G. Tsang

(57) ABSTRACT

Process for improving the quality of a propylene oxide contaminated with poly(propylene oxide), which process comprises the steps of: (a) contacting the liquid propylene oxide with an adsorbent consisting of magnesium silicate and/or calcium silicate under such conditions that the amount of poly(propylene oxide) is reduced to the desired level, and (b) recovering the purified propylene oxide product.

10 Claims, No Drawings

PROCESS FOR THE PURIFICATION OF PROPYLENE OXIDE

This application is a 371 of PCT/EP00/02272 filed Mar. 14, 2000.

The present invention relates to a process for improving the quality of propylene oxide.

Propylene oxide is widely used as precursor for preparing polyether polyols, which upon reaction with polyisocyanate compounds yield polyurethanes. Typically, methods for preparing polyether polyols involve reacting a starting compound having a plurality of active hydrogen atoms with propylene oxide, optionally together with one or more other alkylene oxides like ethylene oxide or butylene oxide. Suitable starting compounds include polyfunctional alcohols, generally containing 2 to 6 hydroxyl groups. Examples of such alcohols are glycols, glycerol, pentaerythritol, trimethylolpropane, triethanolamine, sorbitol, mannitol, etc. Usually a strong base like potassium hydroxide is used as a catalyst in this type of reaction.

The quality of the propylene oxide used to prepare the polyether polyol has significant impact on the quality of the polyurethane foams eventually obtained. Particularly the presence of poly(propylene oxide) is known to cause undesired effects in the polyurethane foam formation. Examples of such undesired effects are the occurrence of blow holes, low foam rise and even collapse of the foam formed. Particularly, in moulding applications the presence of poly(propylene oxide) in the propylene oxide used for preparing the starting polyether polyol may cause problems in terms of quality of the polyurethane foam.

The term "poly(propylene oxide)" as used throughout the present specification refers to poly(propylene oxide) having a molecular weight of 2000 Dalton or higher as determined by polypropylene glycol-calibrated gel permeation chromatography.

Methods for manufacturing propylene oxide are well known in the art. Commercial production normally takes place via the chlorohydrin process or via the hydroperoxide process. In the latter process propene is reacted with an organic hydroperoxide. This hydroperoxide is either tert-butyl hydroperoxide or ethylbenzene hydroperoxide. In the first case tert-butyl alcohol is formed as a co-product (to be further converted into methyl tert-butyl ether), in the second case styrene is formed as the co-product. In the chlorohydrin process chlorine, propene and water are reacted to form propylene chlorohydrin, which is subsequently dehydrochlorinated with calcium hydroxide to form propylene oxide. For the purpose of the present invention it is immaterial which preparation route is used. Namely, in all processes poly(propylene oxide) is formed in undesirably high quantities. Moreover, it is known (e.g. from U.S. Pat. No. 4,692,535) that high molecular weight poly(propylene oxide) may be formed during storage or transport, for example upon contact with a metal, such as carbon steel.

Methods for improving the quality of propylene oxide via adsorption of poly(propylene oxide) are known in the art. Several adsorbents have been reported to be useful for this purpose. For instance, U.S. Pat. No. 4,692,535 discloses the use of activated carbon, charcoal or attapulgite as suitable adsorbents. In EP-A-0,601,273 non-calcined diatomaceous earth is mentioned as adsorbent for removing poly(propylene oxide). In JP-A-08/283253 zeolites and magnesia are mentioned as adsorbents. Suitable zeolites have a pore diameter between 3 and 10 Ångstrom, while the magnesia should suitably consist for at least 90 wt % of magnesium oxide.

Although the known adsorbents, and in particular activated carbon, perform satisfactorily in removing poly(propylene oxide) from propylene oxide, there is still room for improvement. The present invention aims to provide a process for improving the quality of propylene oxide by adsorption, wherein the adsorbent used has at least a similar performance in terms of poly(propylene oxide) removal as activated carbon.

According to U.S. Pat. No. 5,493,035 there are various difficulties associated with using activated carbon as the adsorbent for purifying propylene oxide, particularly during the initial or start-up phase of the activated carbon treatment. The adsorption of propylene oxide onto the activated carbon, namely, is highly exothermic and hence causes excessive temperature increases during said start-up. This has many undesired consequences, one of which is propylene oxide vaporisation and migration in the bed which in return causes secondary exotherms with very high temperatures. This is extremely hazardous and may even cause reactor damage according to U.S. Pat. No. 5,493,035. The solution proposed in U.S. Pat. No. 5,493,035 is a pretreatment of the activated carbon involving contacting this activated carbon with a glycol, such as propylene glycol.

It was envisaged that the adsorbent to be used in the process according to the present invention should not have the above risks associated with the use of activated carbon. On the other hand, the purification performance of the adsorbent to be used should be at least similar to that of activated carbon.

Accordingly, the present invention relates to a process for improving the quality of an propylene oxide contaminated with poly(propylene oxide), which process comprises the steps of:

(a) contacting the liquid propylene oxide with an adsorbent consisting of magnesium silicate and/or calcium silicate under such conditions that the amount of poly(propylene oxide) is reduced to the desired level, and (b) recovering the purified propylene oxide product.

As has already been indicated above, the way in which the propylene oxide is prepared is immaterial to the present invention. Any known preparation process may be applied. The propylene oxide to be treated in the process according to the present invention may be the product directly obtained from the known preparation processes. Alternatively, said directly obtained propylene oxide also may have been subjected to conventional purification and recovery techniques before it is treated in accordance with the present invention. Assuming that the propylene oxide is produced in a hydroperoxide process, such purification and recovery techniques typically involve the removal of unreacted propene and organic hydroperoxide, by-products (like propane, aldehydes and alcohol) and other treating agents. In general, the propylene oxide stream to be treated in the process of the present invention consists for at least 95 wt % of propylene oxide.

The adsorbent is magnesium silicate, calcium silicate or a mixture of both. In principle the known, commercially available magnesium silicates and calcium silicates may be used. Preferred magnesium silicates are the synthetic ones, e.g. prepared by reacting a magnesium salt like magnesium sulphate with sodium silicate. Similarly, synthetic calcium silicates may be used. Typically, the magnesium and calcium silicates are used in their hydrated form, although the dehydrated or water-free silicates may also be used. The use of magnesium silicate as the adsorbent is preferred.

The adsorbent may be used as a powder to form a slurry with the propylene oxide or may be used in extruded form in a bed through which the propylene oxide is passed.

Accordingly, step (a) may in a first embodiment comprise contacting the liquid propylene oxide with a fine powder of the adsorbent. The average particle size of such powder will typically be in the range from 1 to 100 μm, preferably from 2 to 40 μm. Suitably, the adsorbent is dispersed in the liquid propylene oxide yielding a slurry. In this embodiment of the present invention, step (b) advantageously is a filtration step yielding a permeate (or filtrate) containing the purified propylene oxide product. The retentate, consequently, contains the adsorbent with poly(propylene oxide) adsorbed thereon. Filtration may be carried out by microfiltration methods known in the art. The filter used should have such openings that the adsorbent with poly(propylene oxide) adsorbed thereon cannot pass these openings. The exact filter to be used, accordingly, depends on the size of the adsorbent powder particles used. Suitable filters for instance include glass filters, plate filters and multi-tube filters like the Fundabac filters or the Contibac filters (Fundabac and Contibac are trade marks). The multi-tube filters generally comprise a vessel filled with vertically arranged filter elements distributed over a number of compartments, whereby each filter element is a tube of a porous material surrounded by a filter cloth. The slurry is passed through the vessel and the liquid purified propylene oxide is pressed through the filter cloth and the wall of the porous tube into said tube and is recovered at the end of said tube.

The amount of adsorbent used, when the adsorbent is used in powdered form, typically ranges from 0.01 to 20 wt % based on the amount of liquid propylene oxide treated. Preferably, the amount of adsorbent used is in the range of from 0.05 to 15 wt % based on liquid propylene oxide. In general, when using the adsorbent in powdered form, it is preferred to use as little adsorbent as needed to effectively remove poly(propylene oxide), and accordingly it is preferred to use at most 10 wt % and more preferably at most 5 wt % of adsorbent powder. The powder adsorbent may have a surface area of from 10 to 1000 $m^2/g$, but preferably the surface area is at least 50 $m^2/g$, more preferably at least 200 $m^2/g$ and even more preferably at least 400 $m^2/g$.

In an alternative embodiment of the process according to the present invention step (a) comprises passing the contaminated propylene oxide over a bed of shaped particles of the adsorbent. These particles may have any shape conventionally used, including spheres, cylinders, stars, trilobes, quadrulobes, hollow cylinders or monoliths. Their size (diameter) typically is in the order of millimeters, such as from 0.1 to 5 mm. Cylinders typically have a length/diameter ratio of from 2 to 6, preferably 3 to 5. The porosity and surface area of such shaped particles should be such that the poly(propylene oxide) can be adequately adsorbed. A preferred porosity in terms of pore volume is from 0.1 to 3 ml/g, more preferably 0.2 to 2 ml/g and even more preferably 0.5 to 1.2 ml/g as determined by nitrogen adsorption. The surface area may suitably range from 150 to 800 $m^2/g$, more suitably 200 to 600 $m^2/g$ and even more suitably 250 to 500 $m^2/g$ as determined by the BET method (ISO 9277:1995(E)).

In case the particles of the adsorbent material, i.e. magnesium silicate or calcium silicate, are shaped using extrusion, the extrudates will typically comprise a binder material and the adsorbent material. Suitable binder materials include inorganic oxides like silica, magnesia, titania, alumina, zirconia and silica-alumina, of which silica is preferred. The weight ratio of binder to adsorbent material may vary from 10:90 to 90:10, suitably from 20:80 to 50:50.

The extrudates can be made by conventional extrusion techniques known in the art. Typically an extrusion mixture is prepared from powders of the solids (adsorbent and binder) and water by mixing and kneading the ingredients and passing this mixture into the extruder. Such mixture typically has a paste-like appearance. It is within the normal skills of those skilled in the art to optimise the mixing/kneading procedure to obtain an extrudable paste and to select the most appropriate extrusion conditions. Beside the adsorbent material, binder and water the extrusion paste will normally also comprise extrusion aids to improve the flow properties. Such extrusion aids are known in the art and include, for instance, aliphatic mono-carboxylic acids, polyvinyl pyridine, and sulfoxonium, sulfonium, phosphonium and iodonium compounds, alkylated aromatic compounds, acyclic monocarboxylic acids, fatty acids, sulfonated aromatic compounds, alcohol sulfates, ether alcohol sulfates, sulfated fats and oils, phosphonic acid salts, polyoxyethylene alkylphenols, polyoxyethylene alcohols, polyoxyethylene alkylamines, polyoxyethylene alkylamides, polyacrylamides, polyacryl amines, polyols, polyvinyl alcohols, acetylenic glycols and graphite. Burnout materials may also be used to increase the porosity of the final extrudate. Examples of burnout materials are polyethylene oxide, methylcellulose, ethylcellulose, latex, starch, nut shells or flour, polyethylene or any of the polymeric microspheres or microwaxes.

After extrusion the extrudates are dried and calcined. Drying may be effected at an elevated temperature, preferably up to 300° C., more preferably up to 200° C. The period for drying may vary, but will usually up to 5 hours, more suitably from 30 minutes to 3 hours. The drying may also be integrated with the subsequent calcination. Calcination is typically effected at an elevated temperature, preferably up to 1000° C., more preferably from 200 to 800° C., most preferably from 300 to 700° C. Calcination of the extrudates is typically effected for a period of up to 5 hours, preferably from 30 minutes to 4 hours.

Following calcination the extrudates may be subjected to a treatment to neutralise any catalytically active acid sites still present after calcination or possibly formed on the surface of the extrudates during calcination. These acid sites, namely, could potentially promote the formation of poly (propylene oxide). Such treatment could, for example, involve immersing the calcined extrudates in water or subjecting them to a steaming treatment. For the purpose of the present invention a steaming treatment is preferred. Such steaming treatment can be carried out by the conventional methods, for instance, by contacting the calcined extrudates with low pressure steam of 120–180° C. for 30 minutes up to 48 hours, suitably from 2 to 24 hours. If a water immersion or steaming treatment is carried out a drying step under mild conditions (i.e. at 30–100° C.) is carried out.

The extrudates are suitably packed into a fixed bed and the liquid propylene oxide is then passed through this bed. This operation may be repeated several times by recycling the propylene oxide over the adsorbent bed or by passing the propylene oxide through a cascade of two or more fixed bed adsorption columns arranged in series. The purified propylene oxide product is recovered as the bottom stream leaving the adsorption bed or leaving the adsorption bed for the last time (when recycling) or leaving the final bed (when using a cascade of adsorption beds).

One suitable mode of operation is to use two adsorption columns with one column being used as a swing column. In this mode of operation one adsorption column is in operation while the other is bypassed, e.g. for replacement of the adsorbent material. Once the adsorption performance of the adsorbent in the column in operation reaches an undesirable low level, the other adsorption column with fresh adsorbent is taken into operation while the column with the (partly) "deactivated" adsorbent is taken out of operation for replacement of the adsorbent. In this way the adsorption treatment can be very effectively operated. Alternatively, a single adsorption column is used and is temporarily bypassed when the bed needs to be replaced. Given the huge volume of propylene oxide passed over the bed, the poly (propylene oxide) content of the propylene oxide not passed over the adsorption column will be greatly diluted by the large volume of treated propylene oxide. From a process economic perspective this latter option is preferred as it requires only one adsorption column.

The magnesium silicate or calcium silicate adsorbent may be pretreated with an organic liquid to minimise the adsorption heat which is generated when poly(propylene oxide) is adsorbed onto the adsorbent. Although the adsorption heat is already much less than when using activated carbon, a further decrease could be beneficial as it could save on cooling capacity when operating on a commercial scale. In general, cooling equipment is very expensive so if it is possible to dispense with such expensive equipment that would be advantageous. Suitable organic liquids which could be used for this purpose include a glycol, such as propylene glycol, as disclosed in U.S. Pat. No. 5,493,035 (discussed hereinbefore), but preferably an organic liquid selected from ethylbenzene, 1-phenylethanol (methylphenyl carbinol), methylphenyl ketone or a mixture of two or more of these is used. The pretreatment typically involves contacting the adsorbent with the organic liquid for sufficient time to adsorb sufficient organic liquid onto the adsorbent.

The conditions applied in step (a) should preferably be such that the concentration of poly(propylene oxide) is reduced to 0.5 mg/l or less, more preferably to 0.2 mg/l or less. Furthermore, the conditions should be such that the propylene oxide remains in the liquid state. Thus, at atmospheric pressure temperatures from 0° C. up to 34° C. may be applied. Suitably, step (a) is carried out at a temperature in the range of from 5 to 30° C. The pressure is not particularly critical and will normally be in the range of from 0.5 to 10 bar, more suitably from 0.5 to 4 bar. Operating at atmospheric conditions is usually most preferred. The contact time between adsorbent and propylene oxide should be sufficient to achieve the target level of poly(propylene oxide) in the final propylene oxide product. Typically, contact times may vary from 1 minute to several hours, but for practical reasons contact times of 5 minutes to 2 hours are preferred. In a fixed bed operation the liquid hourly space velocity will suitable be from 0.5 to 10 hr$^{-1}$.

The invention is further illustrated by the following examples without limiting the scope of the invention to these particular embodiments.

EXAMPLES

A 250 ml glass reactor with a cooling jacket was charged with 194 g impure propylene oxide. The reactor was placed in an ethylene glycol bath of approximately 15° C. The propylene oxide inside the reactor was stirred at 320 rpm. A sample of 5 g impure propylene oxide was discharged via a P5 boron silicate (i.e. glass) filter (1–1.6 μm) when the propylene oxide reached the desired temperature of about 15° C. and the concentration of poly(propylene oxide) having a molecular weight 2000 Da and higher in this sample was measured ([PPO blank], in mg/l).

The concentration of poly(propylene oxide) was determined by means of combined gel permeation chromatography and evaporative light scattering detection (GPC-ELSD). The ELS detector used was the ALTECH 500 (ALTECH is a trademark), used at 55° C. with a nitrogen flow of 1.9 ml/min. In the GPC-ELSD technique the poly(propylene oxide) having a molecular weight of 2000 Da and higher is separated from lower molecular weight material by means of GPC and is subsequently passed into the ELS detector, where it is nebulized into a fine mist of droplets using nitrogen as the nebulizing gas. The droplets thus -obtained flow through an evaporation tube, where they are partially evaporated leaving clouds of small, non-volatile particles. These particles pass through a light beam and are detected by light scattering on a photo multiplier. The concentration of poly(propylene oxide) can then be calculated from the ELSD peak area found via the relation $$Y=a*C^b$$

wherein Y represents the ELSD peak area, C the poly (propylene oxide) concentration and a and b are constants. The constants a and b were determined from a series of standard solutions of poly(methyl methacrylate) (molecular weight 24,400 Da) with known concentrations.

Example 1

The reactor was charged with impure propylene oxide and a blank PPO was determined as described above.

Subsequently, 0.1% on weight basis of powdered magnesium silicate with a SiO$_2$/MgO molar ratio of 1.5 and containing 17–30% by weight H$_2$O and having an average particle size of 15 μm and a surface area of 500 m$^2$/g was added to the impure propylene oxide under stirring and a slurry was formed. Stirring was continued for 6 minutes. Then about 10 grams of treated propylene oxide was discharged from the reactor vessel via the P5 filter, after which the content of poly(propylene oxide) having a molecular weight of 2000 Da and higher ([PPO], in mg/l) was determined via GPC-ELSD as described above.

The results are indicated in Table 1 (Ex 1).

Comparative Example 1

Example 1 was repeated except that in stead of magnesium silicate 0.1% on weight basis of activated coal was added (CEx 1).

The results are indicated in Table 1.

Example 2

Cylindrically shaped magnesium silicate extrudates having a diameter of 0.8 mm and a length/diameter ratio of from 3 to 4 were prepared as follows.

An extrusion paste was made by mixing and kneading 51 grams of silica powder having a surface area of 200 m$^2$/g, 136 grams of magnesium silicate powder having a surface area of 500 m$^2$/g, 145 grams of water and 9 grams of conventional extrusion aids. This paste was subsequently extruded and the extrusion string with a diameter of 0.8 mm obtained was cut in cylinders with a length of 2.5 to 3 mm.

The shaped extrudates were calcined at 490° C. for 7 hours and subsequently contacted with low pressure steam of 160° C. for 18 hours. The steamed extrudates were dried at 60° C. for 5 hours. The extrudates had a surface area of 348 m²/g (BET method according to ISO 9277) and a pore volume of 0.9 ml/g as determined by nitrogen adsorption.

The reactor was charged with impure propylene oxide and a blank PPO was determined as described above.

Subsequently, 1% on weight basis of the shaped magnesium silicate extrudates prepared as described above was added to the impure propylene oxide under stirring and a slurry was formed. Stirring was continued for 60 minutes. Then about 10 grams of treated propylene oxide was discharged from the reactor vessel via the P5 filter, after which the content of poly(propylene oxide) having a molecular weight of 2000 Da and higher ([PPO], in mg/l) was determined via GPC-ELSD as described above.

The results are indicated in Table 1 (Ex 2).

Comparative Example 2

Example 2 was repeated except that in stead of magnesium silicate 1% on weight basis of activated coal extrudates were used.

The results are indicated in Table 1 (CEx 2).

TABLE 1

Purification of propylene oxide

| Example | [PPO blank] (mg/l) | [PPO] (mg/l) |
| --- | --- | --- |
| Ex 1 | 2.0 | 0.0 |
| CEx 1 | 2.3 | 1.5 |
| Ex 2 | 2.4 | 0.2 |
| CEx 2 | 2.2 | 0.0 |

From Table I it can be seen that using magnesium silicate as adsorbent in very small amounts (only 0.1 wt %) results in removal of all poly(propylene oxide) from the impure propylene oxide (Example 1), whereas using the same amount of activated carbon results in a worse performance of the adsorbent in terms of poly(propylene oxide) removal (Comparative Example 1). When using magnesium silicate in extruded form and at a level of 1 wt % (Example 2), the adsorption performance is similar to the adsorption performance when using the same amount of activated carbon extrudates (Comparative Example 2).

Example 3

In this example the adsorption of poly(propylene oxide) on magnesium silicate extrudates was carried out under adiabatic conditions to determine the effect of the adsorbent used on the adsorption heat released.

An adiabatic pressure Dewar provided with a calorimeter (AISI-304 ADC II ex Chilworth) was loaded with 140 grams of the magnesium silicate extrudates used in example 2 and a nitrogen atmosphere was applied. Propylene oxide was supplied from a steel 160 ml bombe at room temperature (20° C.) using an overpressure of 4 bar nitrogen. Total pressure in the Dewar amounted to 2 bara. The amount of propylene oxide supplied corresponded with the total volume of void fraction and pore volume of the magnesium silicate extrudates present, thereby simulating a completely filled adsorption bed.

A thermocouple was present in the center of the adsorbent bed to measure the temperature. The Dewar was allowed to stand for 24 hours.

The amounts of the various components added and the temperature differential recorded ($\Delta T$) are indicated in table 2.

Examples 4 and 5 and Comparative Example 3

Example 3 was repeated except that:

the magnesium silicate extrudates were pretreated with 100 grams of ethylbenzene (Example 4) or with 117 grams of a 70/30 w/w mixture of methylphenyl ketone and methylpenyl carbinol (Example 5), or 0.8 mm activated carbon extrudates (NORIT RO 0.8; NORIT is a trademark) were used instead of magnesium silicate extrudates.

The amounts of adsorbent and propylene oxide (PO) added and the temperature differential recorded ($\Delta T$) are indicated in table 2.

TABLE 2

Adsorption heat

| | adsorbent (g) | PO (g) | ($\Delta T$) (° C.) |
| --- | --- | --- | --- |
| Example 3 | 140 | 149 | 6.4 |
| Example 4 | 140 | 149 | 2.1 |
| Example 5 | 140 | 149 | −0.5 |
| Comp. Ex. 3 | 100 | 172 | 20.5 |

Table 2 shows that the activated carbon adsorbent releases the highest amount of adsorption heat and hence causes the highest temperature raise. The magnesium silicate extrudates clearly release much less adsorption heat than the activated carbon extrudates. The release into the environment of adsorption heat is even further lowered when pretreating the magnesium silicate with ethylbenzene or with a mixture of methylphenyl ketone and methylphenyl carbinol. It is believed that this is inter alia caused by the solvent used acting as a heat sink for the adsorption heat and in case of Example 5 by an additional endothermic heat effect due to mixing the solvent used with propylene oxide. It will be appreciated that a major advantage of a low or minimal release of adsorption heat is that cooling can be minimised or even be completely dispensed with. This is very attractive from a process economics perspective.

What is claimed is:

1. A process for improving the quality of an propylene oxide contaminated with poly(propylene oxide), which process comprises the steps of:

(a) contacting the liquid propylene oxide with an adsorbent selected from the group consisting of magnesium silicate and calcium silicate under such conditions that the amount of poly(propylene oxide) is reduced to the desired level, and (b) recovering the purified propylene oxide product.

2. The process as claimed in claim 1, wherein step (a) comprises contacting the liquid propylene oxide with a powder of the adsorbent, wherein the average particle size of which powder is in the range from about 1 to about 100 μm.

3. The process as claimed in claim 2, wherein the adsorbent is dispersed in the liquid propylene oxide yielding a slurry.

4. The process as claimed in claim 2, wherein step (b) comprises a filtration step yielding a permeate containing the purified propylene oxide product.

5. The process as claimed in claim 2, wherein the amount of adsorbent used is in the range of from about 0.05 to about 15 wt % based on liquid propylene oxide.

6. The process as claimed in claim 1, wherein step (a) comprises passing the contaminated propylene oxide over at least one bed of extrudates of the adsorbent.

7. The process as claimed in claim 1, wherein the adsorbent is pretreated with an organic liquid.

8. The process as claimed in claim 7, wherein the organic liquid is selected from the group consisting of ethylbenzene, methylphenyl carbinol, ethylphenyl ketone and a mixture of two or more of these.

9. The process as claimed in claim 1, wherein the conditions applied in step (a) are such that the concentration of poly(propylene oxide) is reduced to about 0.5 mg/l or less.

10. The process as claimed in claim 1, wherein step (a) is carried out at a temperature in the range of from about 5 to about 30° C.

* * * * *